United States Patent

Matula et al.

Patent Number: 5,551,448
Date of Patent: Sep. 3, 1996

[54] ENDOSCOPIC SURGICAL INSTRUMENT FOR ASPIRATION AND IRRIGATION

[75] Inventors: Paul A. Matula, Brookfield; William J. McCabe, New Canaan, both of Conn.; Gerald T. McCourtney, Orono, Minn.; Dennis Gemmell, Robinsdale, Minn.; Jerry Hamlin, Golden Valley, Minn.; Graeme Winslow, Excelsior, Minn.

[73] Assignee: United States Surgical Corporation, Norwalk, Conn.

[21] Appl. No.: 278,560

[22] Filed: Jul. 21, 1994

Related U.S. Application Data

[63] Continuation of Ser. No. 906,673, Jun. 30, 1992, abandoned, which is a continuation-in-part of Ser. No. 781,062, Oct. 18, 1991, abandoned.

[51] Int. Cl.$^6$ .................................................. B65D 83/00
[52] U.S. Cl. .................................................. 128/897
[58] Field of Search ........................... 206/486, 373, 206/372, 370, 63.5, 438; 128/897

[56] References Cited

U.S. PATENT DOCUMENTS

| | | |
|---|---|---|
| 1,740,174 | 12/1929 | Hevern . |
| 2,193,164 | 3/1940 | Cochran ................... 221/121 |
| 3,456,817 | 7/1969 | Irazoqui ................... 221/122 |
| 3,527,203 | 9/1970 | Gravlee . |
| 3,564,662 | 2/1971 | Dold ........................ 206/370 |
| 3,613,901 | 10/1971 | Montelius ................. 211/163 |
| 3,809,977 | 5/1974 | Bolamuth et al. ......... 206/370 |
| 3,929,126 | 12/1975 | Corsaut . |
| 3,994,297 | 11/1976 | Kopf . |
| 4,120,397 | 10/1978 | Neumann . |
| 4,132,227 | 1/1979 | Ibe . |
| 4,149,315 | 4/1979 | Page, Jr. et al. . |
| 4,306,862 | 12/1981 | Knox ........................ 433/77 |
| 4,320,761 | 3/1982 | Haddad . |
| 4,342,391 | 8/1982 | Schainholz ............... 206/370 |
| 4,423,727 | 1/1984 | Widran et al. . |
| 4,448,307 | 5/1984 | Roggenkamp ........... 206/369 |
| 4,493,694 | 1/1985 | Wuchinich . |
| 4,517,962 | 5/1985 | Heckele . |
| 4,573,965 | 3/1986 | Russo . |
| 4,586,614 | 5/1986 | Ger ........................... 206/370 |
| 4,657,016 | 4/1987 | Garito et al. . |
| 4,717,380 | 1/1988 | Baumgartner . |
| 4,737,142 | 4/1988 | Heckele . |
| 4,744,360 | 5/1988 | Bath . |
| 4,746,016 | 5/1988 | Pollak et al. ............. 206/370 |
| 4,747,820 | 5/1988 | Hornlein et al. . |
| 4,769,018 | 9/1988 | Wilson . |
| 4,776,840 | 10/1988 | Freitas et al. . |
| 4,846,790 | 7/1989 | Hornlein et al. . |
| 4,881,523 | 11/1989 | Heckele . |
| 4,886,491 | 12/1989 | Parisi et al. . |

(List continued on next page.)

FOREIGN PATENT DOCUMENTS

| | | |
|---|---|---|
| 0463363 | 1/1992 | European Pat. Off. . |
| WO9003152 | 4/1990 | WIPO . |
| WO9200705 | 1/1992 | WIPO . |

OTHER PUBLICATIONS

Cabot Medical Corporation "Introducing the Corson Disposable Suction/Irrigation Probe", Copyright 1990.

Primary Examiner—Manuel Mendez

[57] ABSTRACT

An endoscopic surgical instrument for aspiration and irrigation of a surgical site. The device inclues at least one rotatable trumpet valve to provide for variable oreintation of the device during use. Connection ports for connection to irrigation fluid and a suction source are provided which communicate with a single lumen cannula which transports both the irrigation fluid and the suction pressure to the surgical site. The single lumen cannula is provided with a sleeve to vary the pressure of the irrigation fluid to provide for high pressure application of the irrigation fluid to perform hydrodissection. A plurality of dissector tips and a novel mechanism for securing the tips to the single lumen cannula are also dislcosed. Also disclosed is a novel dispensing device for the tips and a kit which includes the tip dispenser and an endoscopic surgical instrument.

22 Claims, 18 Drawing Sheets

U.S. PATENT DOCUMENTS

| | | |
|---|---|---|
| 4,898,574 | 2/1990 | Uchiyama et al. . |
| 4,921,476 | 5/1990 | Wuchinich . |
| 4,921,477 | 5/1990 | Davis . |
| 4,922,902 | 5/1990 | Wuchinich et al. . |
| 4,924,851 | 5/1990 | Ognier et al. . |
| 4,931,047 | 6/1990 | Broadwin et al. . |
| 4,956,907 | 9/1990 | Bruno ............... 128/919 |
| 4,959,058 | 9/1990 | Michelson . |
| 4,968,306 | 11/1990 | Huss et al. . |
| 5,026,386 | 6/1991 | Michelson . |
| 5,053,002 | 10/1991 | Barlow . |
| 5,084,028 | 1/1992 | Kennedy et al. ............... 128/919 |
| 5,085,658 | 2/1992 | Meyer . |
| 5,152,422 | 10/1992 | Springer ............... 221/121 |
| 5,156,607 | 10/1992 | Kansas . |
| 5,174,447 | 12/1992 | Fleming ............... 206/373 |
| 5,195,958 | 3/1993 | Phillips . |
| 5,199,565 | 4/1993 | Voroba ............... 221/122 |
| 5,212,362 | 5/1993 | Burden et al. ............... 128/919 |
| 5,215,212 | 6/1993 | Stephan ............... 221/87 |
| 5,226,536 | 7/1993 | Elliot ............... 206/486 |
| 5,242,426 | 9/1993 | Pituch ............... 604/263 |

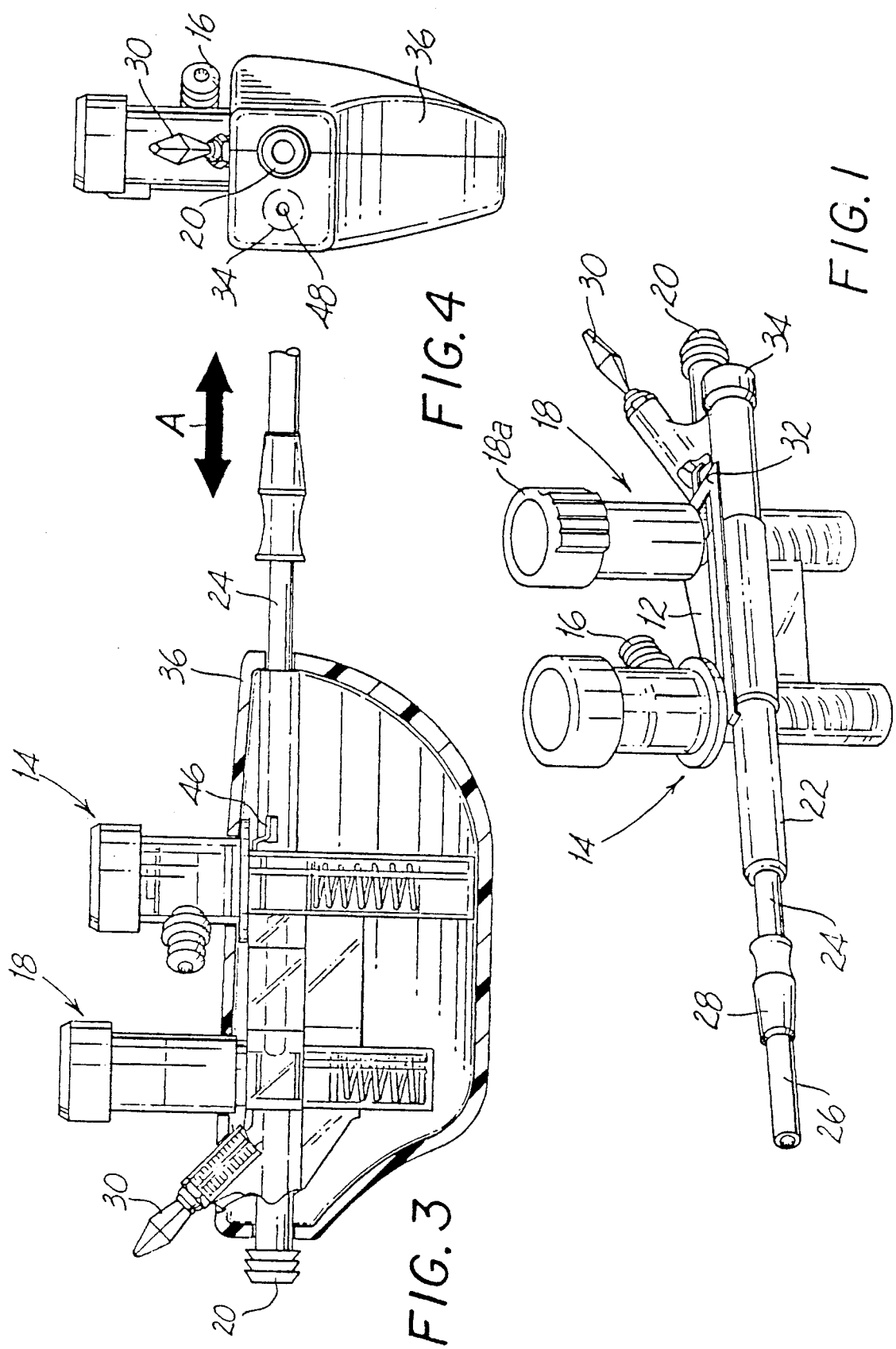

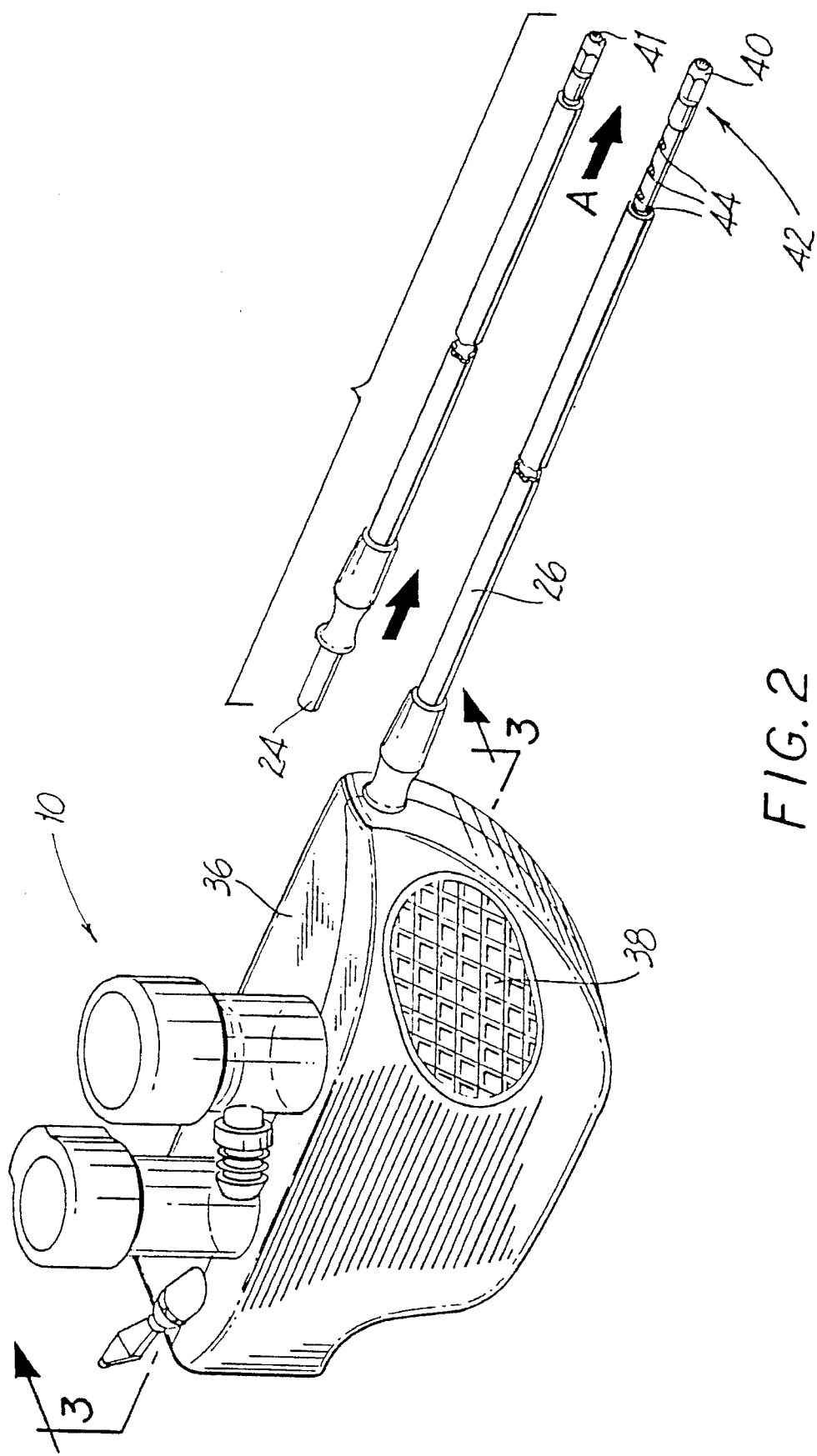

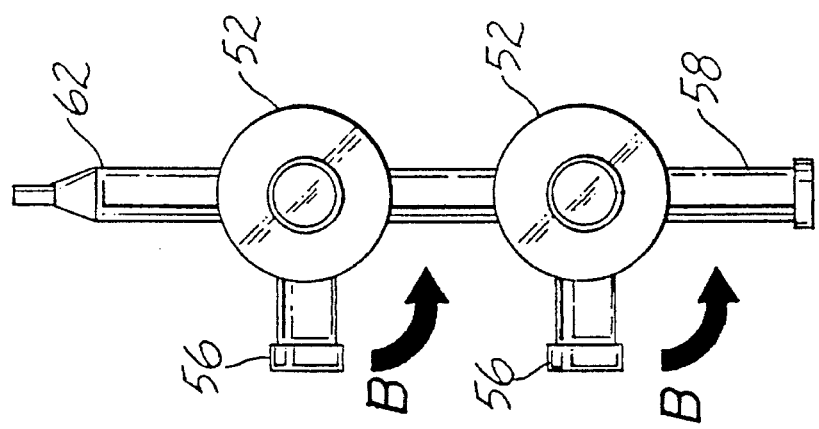
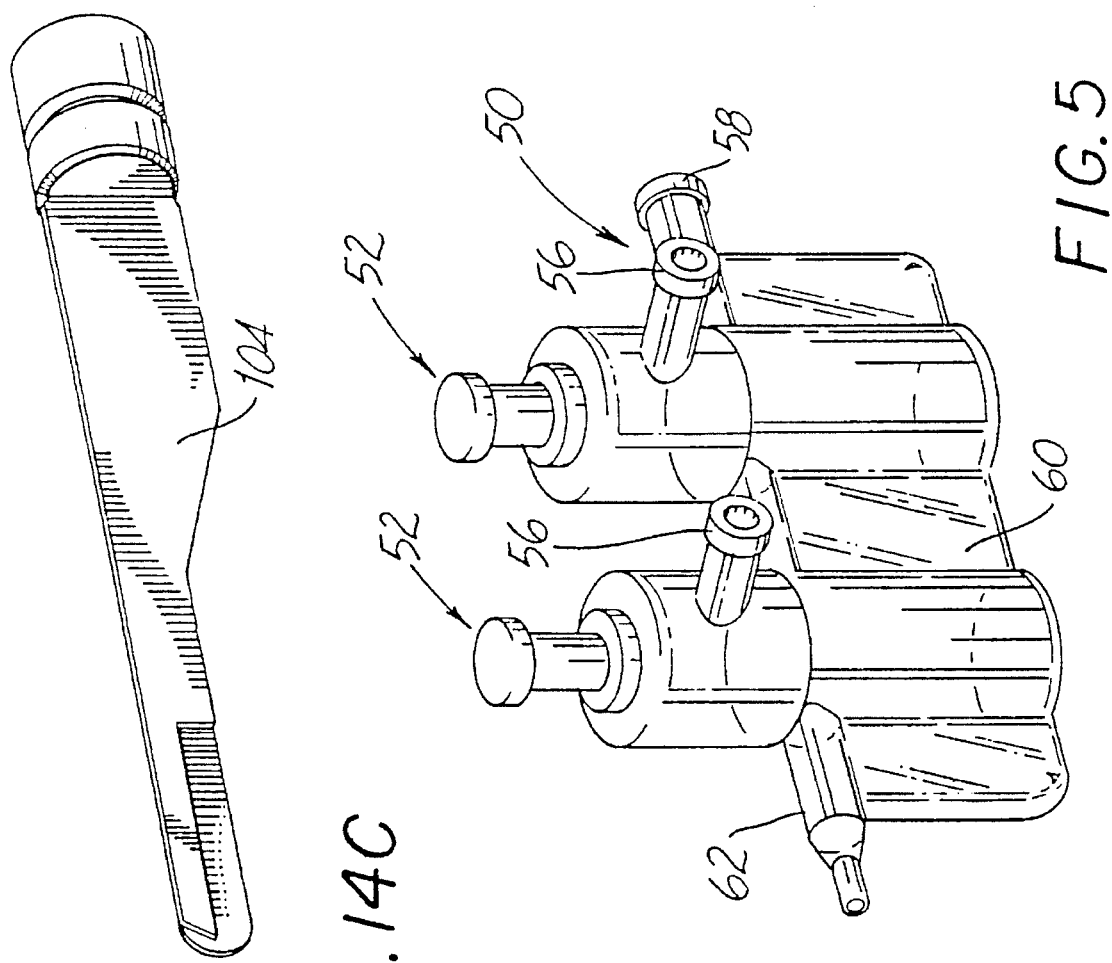
FIG.6
FIG.5
FIG.14C

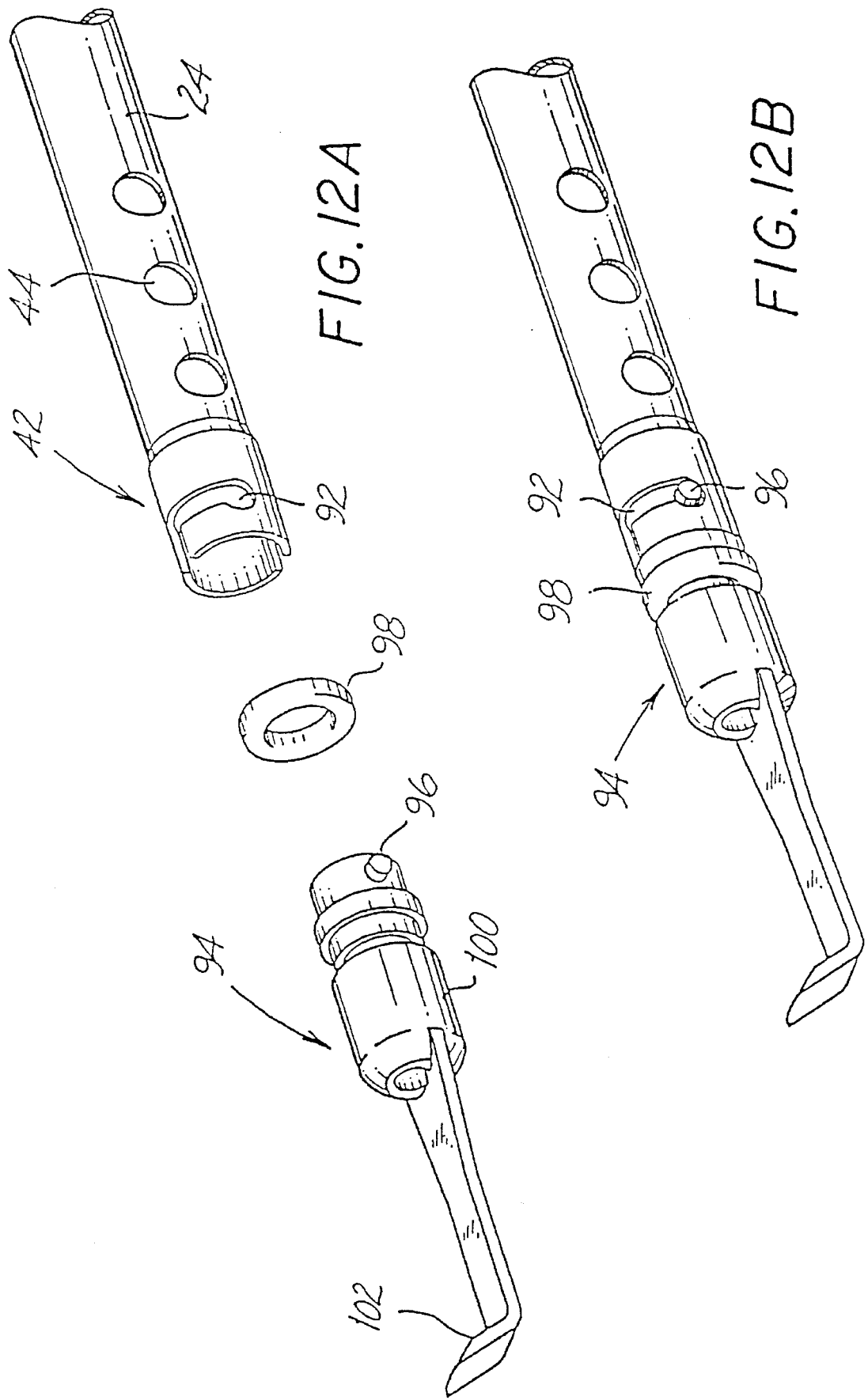

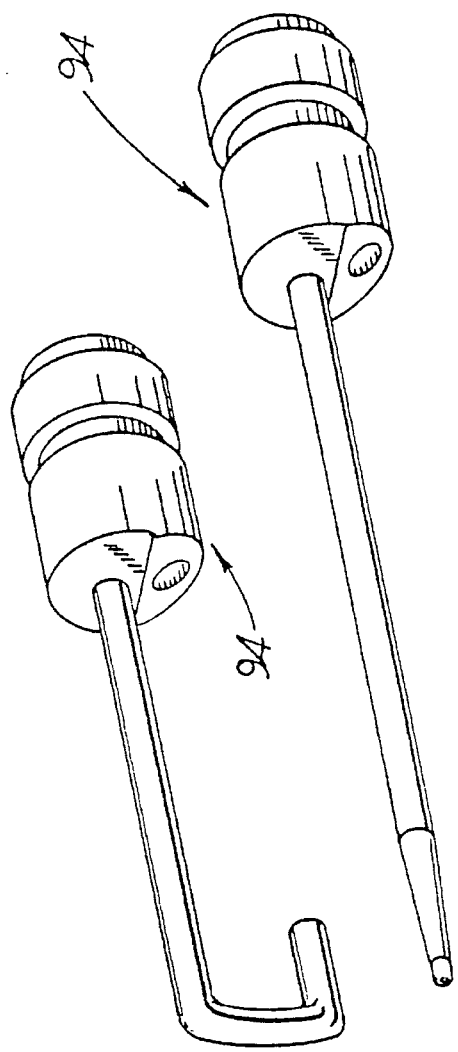
FIG.13A
FIG.13B
FIG.13C
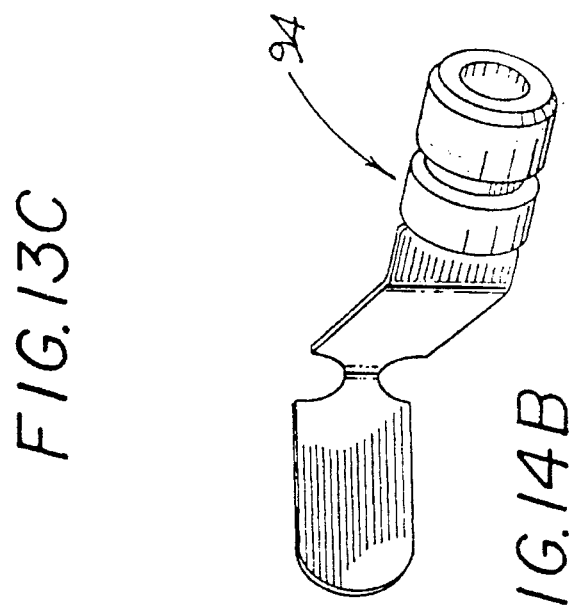
FIG.14B
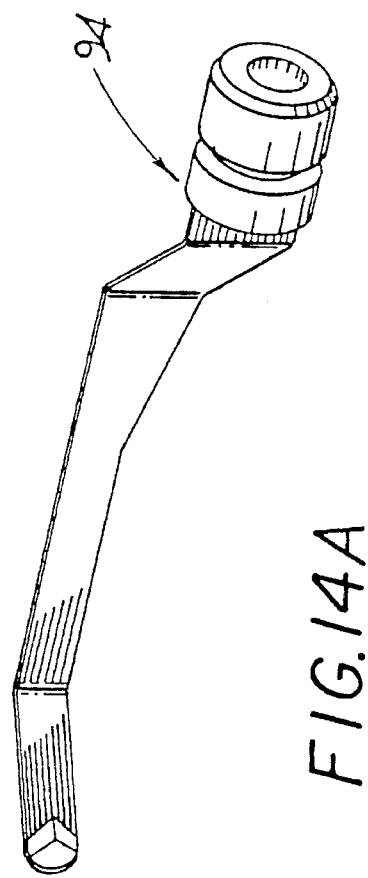
FIG.14A

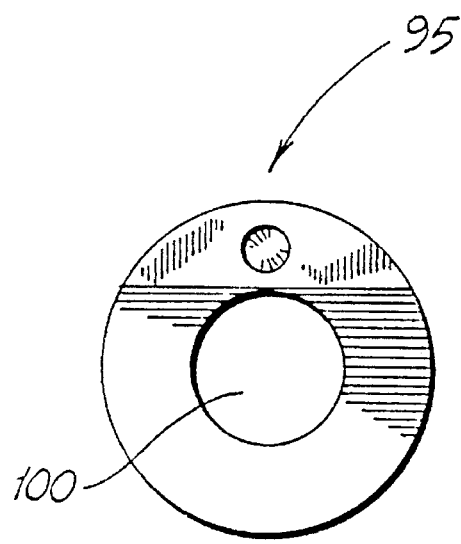
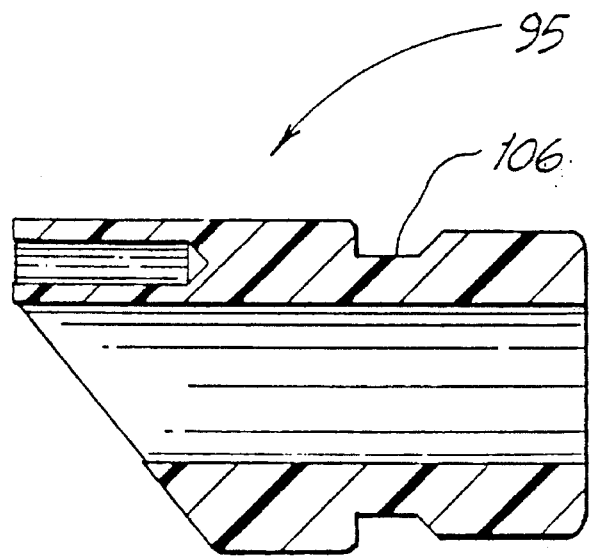
FIG.15A    FIG.15B
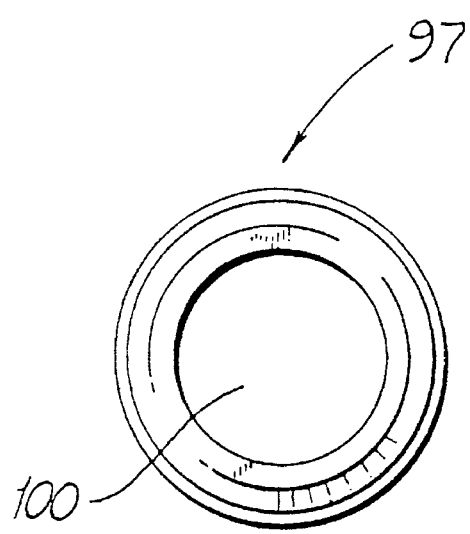
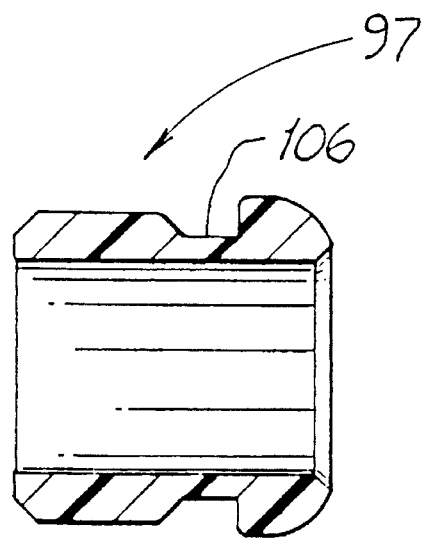
FIG.16A    FIG.16B

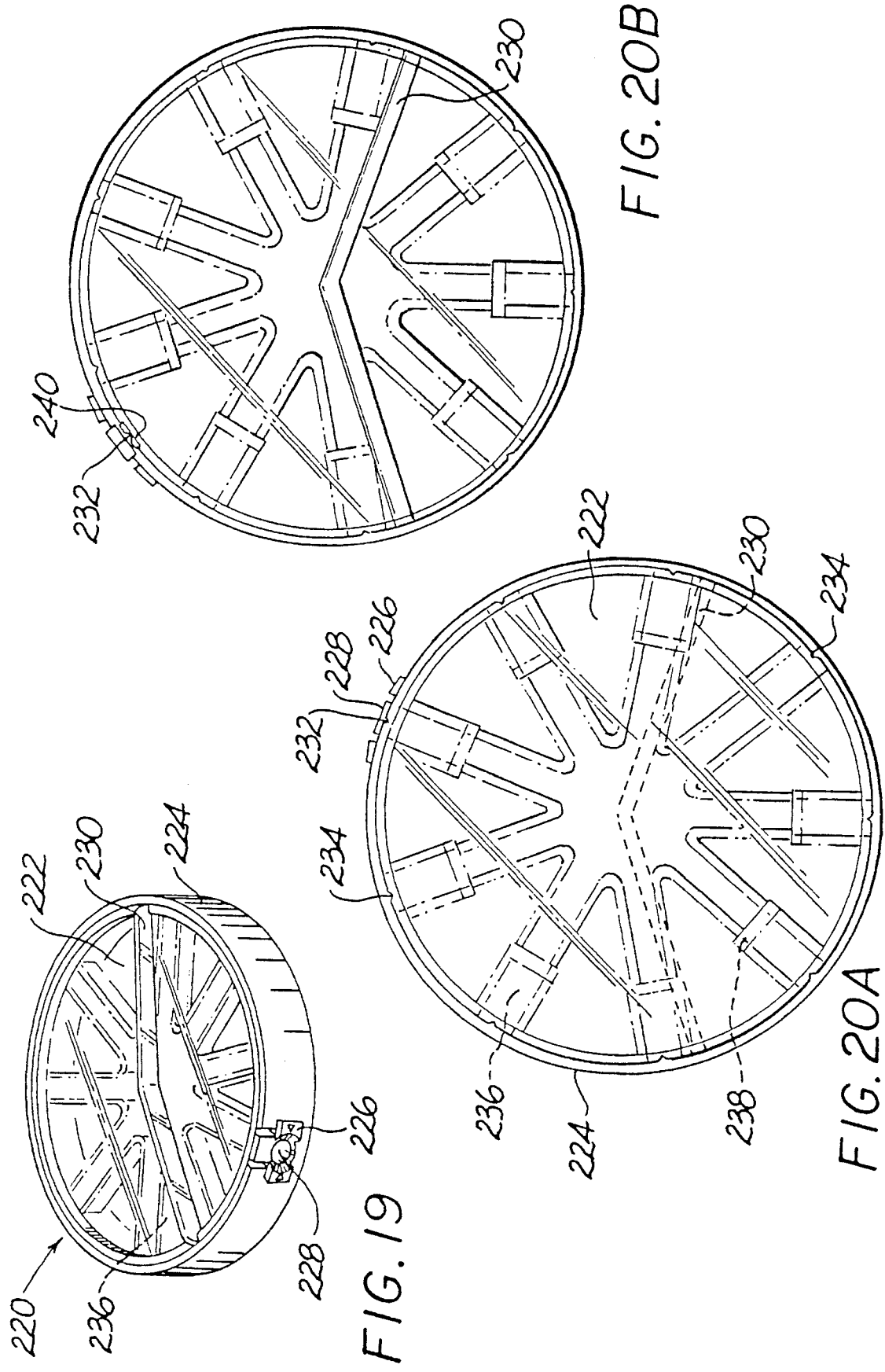

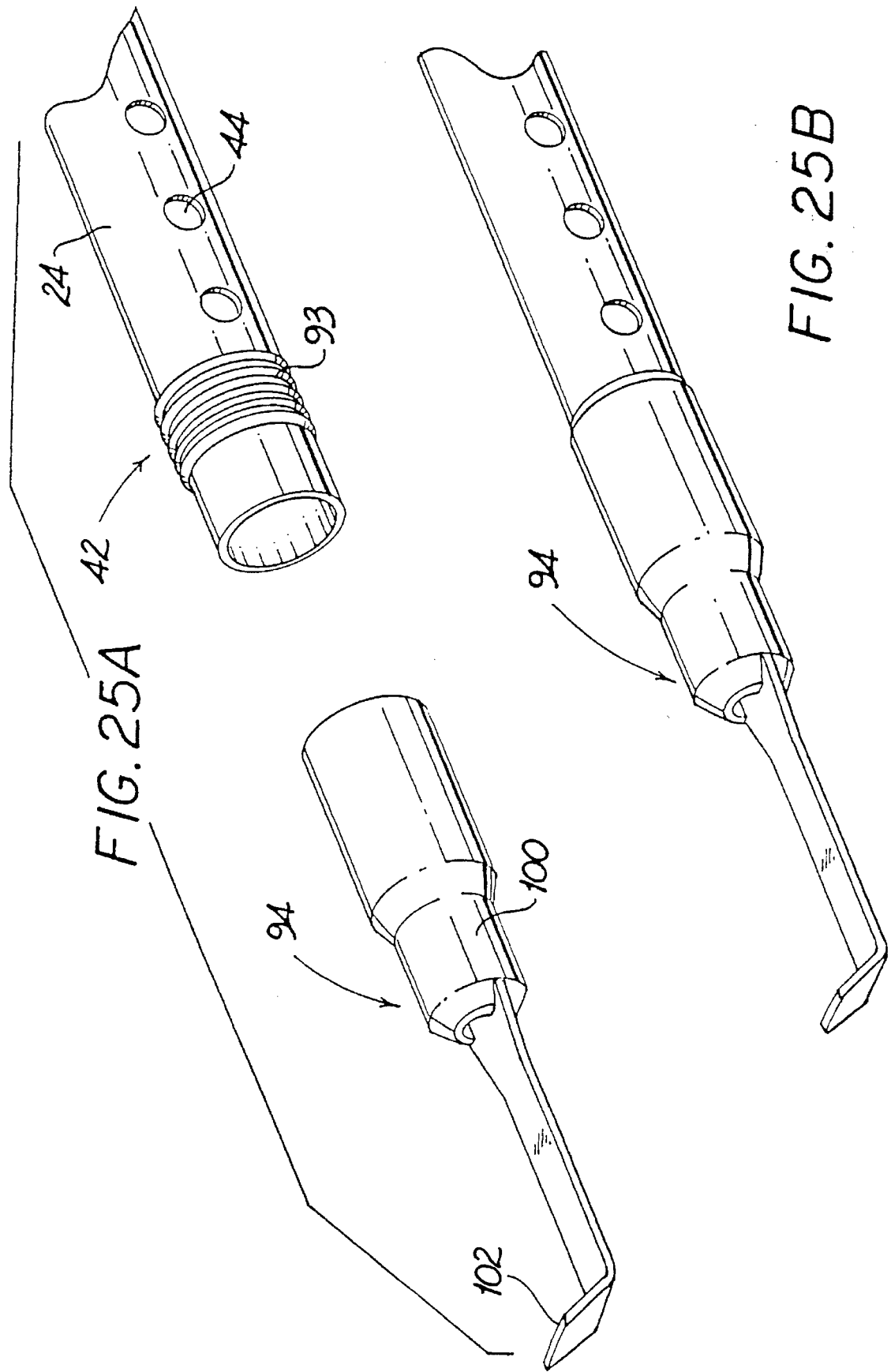

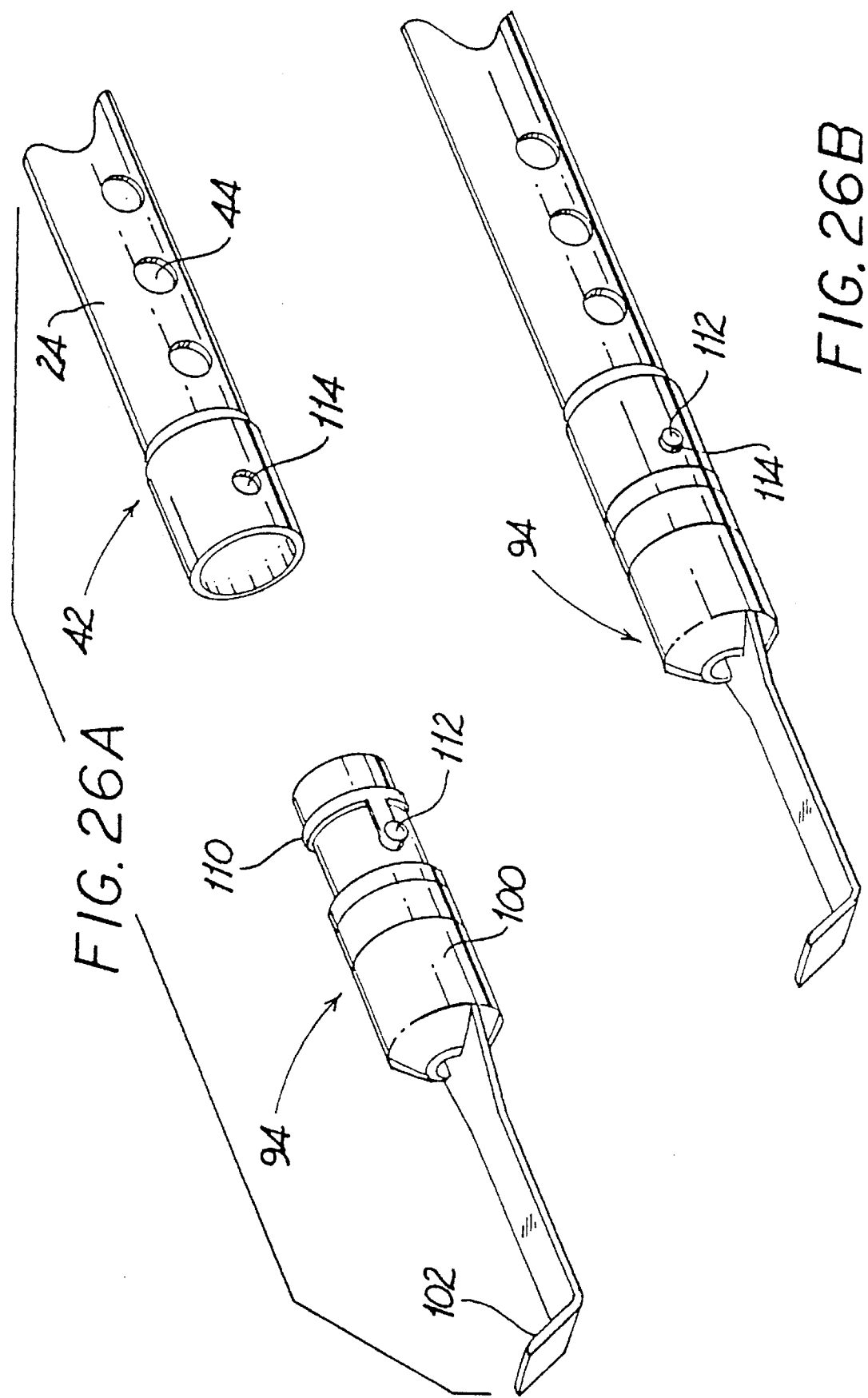

ENDOSCOPIC SURGICAL INSTRUMENT FOR ASPIRATION AND IRRIGATION

This is a continuation of application Ser. No. 07/906,673 filed on Jun. 30, 1992, now abandoned, which is a continuation-in-part of application Ser. No. 07/781,062 filed on Oct. 18, 1989, now abandoned.

BACKGROUND OF THE INVENTION

1. Field of the Invention

The present invention relates to endoscopic surgical instruments, and more particularly to endoscopic surgical instruments for aspirating and irrigating a surgical site having a plurality of interchangeable tool tip members for performing surgical procedures.

2. Discussion of the Prior Art

Surgical devices for providing irrigation fluid and suction to a surgical site to irrigate and evacuate the tissue in the area on which the surgical procedure is being performed are well known in the art. Several of these devices provide a handle member having switching means for turning on and off the flow of the fluid stream and the suction means, and typically connect the suction source and the fluid source to an elongated flexible tubular member which is positioned adjacent the surgical site. In many instances, the tube or catheter is comprised of a complex series of passages which provide a separate channel for the irrigation fluid and a separate channel for the suction means. Several devices provide a pump source to provide the fluid under pressure; however, other devices provide a source of irrigation fluid which is operable under head pressure to gently wash the tissue. The prior art devices typically provide a large tube or catheter which enclose the several channels to deliver the fluid and provide the suction during oral surgery, or invasive surgery which allows for the positioning of the cumbersome tubing.

Several of the prior art devices provide numerous features including electrocautery, laser dissection, and viewing capabilities, all through a single tool member disposed at the operative distal end of the device. Typically, the handle grip includes on/off switches in the form of trumpet valves which allow the surgeon to selectively choose the suction or irrigation feature. Many devices provide a pistol type hand grip which allows the surgeon to operate the device with the thumb-actuated valves. Other devices provide tubular connections such as Luer-type connectors to couple the irrigation source or the suction source to the catheter or tube.

With the recent developments in endoscopic and laparoscopic surgical procedures, it is necessary to provide a device in which many of the functions provided by the more complex and cumbersome prior art devices are included in a streamlined construction in which many of the features are provided in a single unit. In laparoscopic and endoscopic surgical procedures, a small incision or puncture is made in the patient's body to provide access for a tube or cannula device. The cannula is inserted into the patient's body through the provision of a trocar assembly which further includes an obturator for penetrating the body wall. After the obturator is removed, the cannula remains in place to maintain access to the surgical site. Once the cannula is in place, the surgical instrument may be inserted through the cannula to perform the procedure, while the surgical area is viewed through an endoscope or a miniature camera inserted through secondary cannulas to display the procedure on a video monitor.

The prior art devices are subject to several disadvantages when considered for use in laparoscopic or endoscopic surgical procedures. The primary focus behind such surgical procedures is that the surgery is minimally invasive to the patient's body, consequently reducing damage to surrounding tissue and organs and reducing the scarring resulting from the operation, which, as a result, greatly reduces recovery time for the patient. The prior art devices, which typically provide a plurality of channels in the tube or catheter portion to transport the suction and irrigation means to the surgical site, are generally provided for invasive type surgery which allows the larger diameter catheters to be manually positioned adjacent the surgical objective through large incisions.

A further limitation to which the prior art devices are subjected involves positioning of the device during the surgical procedure. Many of these devices are provided with a pistol-type grip which requires a particular orientation of the device in relation to the surgeon's position during the procedure. Should it become necessary for the device to be relocated during the surgical procedure, it is often times uncomfortable to the surgeon to position the device at an angle that does not facilitate operation of the valve members to turn the various features on and off. As a result, the effectiveness of the device is limited, and in many times requires a surgical assistant to operate the device for the surgeon.

Typical suction and irrigation devices having a hand grip in the shape of a pistol are disclosed in U.S. Pat. No. 4,149,315 to Page, Jr. et at. and U.S. Pat. No. 4,776,840 to Freitas et al. Page, Jr. et at. provides a dental suction/irrigation device which includes an elongated tube member which transports the suction means and the irrigation means to the tissue site. The elongated tubular member comprises a pair of concentric tubes where the inner tube provides the irrigation fluid and the outer tube is provided for the suction. A pair of trumpet valves are provided to actuate the irrigation source and the aspiration source. Freitas et al. discloses a similar device but includes a complex internal manual pump to provide the irrigation fluid. A second flexible tube is provided for a vacuum source to evacuate fluid and gases from the surgical site.

U.S. Pat. No. 4,744,360 Bath provides a surgical device for removing cataract lenses which includes an optical fiber for laser surgery which is surrounded by an irrigation sleeve and a separate aspirator sleeve which provides fluid for irrigation and suction for evacuation, respectively, of the surgical site.

A Cabot Medical Corporation brochure (copyright 1990) discloses a suction/irrigation probe which includes a hydrodissection insert which comprises a rod which passes through the tube of the suction/irrigation probe to adjust the flow of the irrigation fluid.

Other known devices include U.S. Pat. No. 4,921,476 and U.S. Pat. No. 4,493,694 to Wuchinich, and U.S. Pat. No. 3,527,203 to Gravlee, which include a tube having several channels for carrying the irrigation fluid separately from the suction device.

A further disadvantage to the devices known in the prior art lies in the fact that the operative end of the device includes only one, non-changeable tool member, if a tool member is provided at all. Typically, suction and irrigation devices terminate in an open tube member for aspirating or irrigating the surgical site. Those devices which do provide a tool at the operative end generally have a permanent member in position, so that the surgeon must change instruments in the event a different tip is required. Some prior art devices have interchangeable tool members, however each tool is attached to a different tubular member so that the entire tubular member needs to be replaced. This causes difficulty in changing tools due to the maneuvering and hand manipulation required to switch tubular members, and further increases the expense of the instruments.

The novel endoscopic surgical device for suction and irrigation of tissue during a surgical procedure obviates the disadvantages encountered in the prior art and provides a compact instrument which includes many of the features necessary to perform the surgical procedure, and which is dimensioned to fit through a cannula for the performance of endoscopic or laparoscopic surgical procedures. The device of the present invention allows a surgeon to operate the suction and irrigation device with either hand and at any orientation to the surgical site comfortably and without assistance, and further allows the surgeon to expand the surgical procedure through the provision of a plurality of interchangeable tool tip members for quick connection to the surgical device. The tool tips preferably are provided in an indexable case to allow the surgeon to choose the right tool tip for the required surgical procedure.

SUMMARY OF THE INVENTION

The present invention provides a novel irrigation and aspiration device for performing endoscopic or laparoscopic surgical procedures which allows the surgeon to operate the device with either hand and at any orientation to the patient's body. The device includes numerous features necessary for the performance of a surgical procedure such as dissection of tissue, or to provide suction and irrigation to a surgical site where the procedure is performed with additional instruments. The present invention further provides a plurality of interchangeable tip members which may be freely substituted at the operative end of the device by the surgeon depending on the procedure being performed. The tips preferably are packaged in an indexable case, which provides sterile and efficient access to the tips by the surgeon.

The suction and irrigation device of the present invention comprises a variably orientable subassembly which may be incorporated into various outer enclosures or housings dependent on the surgeon's preference and on the type of surgical procedure in which the surgical instrument is to be used. The subassembly essentially comprises a connection port for a source of suction and means to actuate the source of suction through the port, as well as a connection point for irrigation fluid with means to actuate the irrigation source through the port. A single lumen cannula is provided which communicates with the actuating means for both the suction port and the irrigation port which transports the suction means and the irrigation fluid to the surgical site. The device may further include a port for an optical fiber for the performance of laser surgery which further communicates with the single lumen cannula to locate the optical fiber through the cannula to the surgical site. Furthermore, electrocautery means may be provided for the performance of cauterization procedures at the surgical site.

The single lumen cannula is provided with a connection means at its distal end for the interchangeable connection of various operative tips which allows the surgeon to perform various surgical procedures. These tips include, among others, a surgical knife, blunt dissectors, retractors, spatulas, and a nozzle for high pressure hydrodissection. The cannula is provided with a plurality of apertures at the distal end for communicating the interior of the cannula with the surrounding environment at the surgical site.

It is often necessary during a surgical procedure for a surgeon to change the tool mechanism at the surgical site. In many instances, the change of tools must be done quickly in order to minimize trauma at the site. In the past, it was often necessary to provide a multitude of surgical instruments or tubular members with tools attached in order to be properly prepared for whatever may arise during the operation. A need therefore exists for the provision of a single instrument having interchangeable tip members at the operative end to provide a convenient and quick to use multi-surgical instrument.

To this end, the present invention further provides a dispenser for the tool tip members to allow the surgeon to choose the proper tip for the required surgical operation. The dispenser may hold a plurality of tips and includes means for dispensing the tips to the surgeon as well as means to retain the remaining tips. The means for dispensing includes means for inserting the surgical device into the dispenser to snap on the tip member, so that sterility is maintained and the surgeon may quickly and efficiently access the tips. It is also contemplated that the dispenser and suction/irrigation device be packaged together as a kit, to enable the surgeon to have the proper tip members on hand during the operation.

A further feature of the device is the hydrodissection capability, in which the high pressure fluid may be directed to the tissue at high pressure to dissect the tissue. In this regard, a concentric outer sleeve member is provided along the length of the cannula which is longitudinally slidable to cover one or all of the apertures at the distal end of the cannula. This allows the surgeon to vary the pressure and provides a visual indication for adjusting the pressure at the distal end.

A further feature of the present invention is the variably orientable valve members which allows the surgeon to operate the device with either hand and at any orientation in relation to the patient's body. Preferably, the optical fiber connection port is axially aligned with the longitudinal axis of the single lumen cannula. At least one of the connection ports for either the aspiration means or the suction means, or both, includes a rotatable trumpet valve to allow the surgeon to rotate the valve at least 180° from one position perpendicular to the longitudinal axis of the single lumen cannula to a second position perpendicular to the longitudinal axis of the single lumen cannula on the opposite side of the cannula. If one connection port is rotatable, the other may be rotatable, or may extend from the distal end of the device so that the connection port is within substantial parallel alignment with the longitudinal axis of the single lumen cannula and the laser optical fiber connection port. Furthermore, the connection for the electrocautery feature preferably includes a bayonet-type male connector which extends at an angle to, but generally in the same direction as, the longitudinal axis of the single lumen cannula. These features allow the surgeon to vary the orientation of the device and operate the device with either hand by rotating the trumpet valves so that the tubes or hoses which deliver the suction means or the irrigation fluid are in an unobstructed position.

BRIEF DESCRIPTION OF THE DRAWINGS

The foregoing features of the present invention will become more readily apparent and may be understood by referring to the following detailed description of the encloseopic surgical aspiration and irrigation instrument, taken in conjunction with the accompanying drawings, in which:

FIG. 1 illustrates a perspective view of the subassembly of the endoscopic surgical instrument for aspiration and irrigation according to the present invention;

FIG. 2 illustrates a perspective view of the present invention including an external housing according to a first embodiment;

FIG. 3 illustrates a side plan view in partial cross section of the embodiment of FIG. 2;

FIG. 4 illustrates a rear plan view of the device of FIG. 2;

FIG. 5 illustrates a perspective view of a second embodiment of the subassembly of the endoscopic surgical instrument for aspiration and irrigation according to the present invention;

FIG. 6 illustrates a top plan view of the device of FIG. 5;

FIGS. 12a and 12b illustrate an exploded perspective view and a perspective view, respectively, of the distal end of the single lumen cannula having a dissector tool mechanism attached thereto by a bayonet-type clip;

FIGS. 13a through 13c illustrate various electrocautery dissectors for use with the device of the present invention;

FIGS. 14a through 14c illustrate various blunt dissectors and surgical knives for use with the device of the present invention;

FIGS. 15a and 15b illustrate a coupling member for use with the dissectors of FIGS. 13a through 13c;

FIGS. 16a and 16b illustrate a coupling member for use with the dissectors of FIGS. 14a through 14c;

FIG. 19 illustrates a perspective view of a second embodiment of a tip dispenser according to the present invention;

FIG. 20a illustrates top plan view of the dispenser of FIG. 19;

FIG. 20b illustrates a bottom plan view of the dispenser of FIG. 19;

FIGS. 25a and 25b illustrate an exploded perspective view and a perspective view, respectively, of the distal end of the single lumen cannula having a tool mechanism attached thereto by screw threads;

FIGS. 26a and 26b illustrate an exploded perspective view and a perspective view, respectively, of the distal end of the single lumen cannula having a tool mechanism attached thereto by a spring clip.

DETAILED DESCRIPTION OF THE PREFERRED EMBODIMENTS

Figure 7:
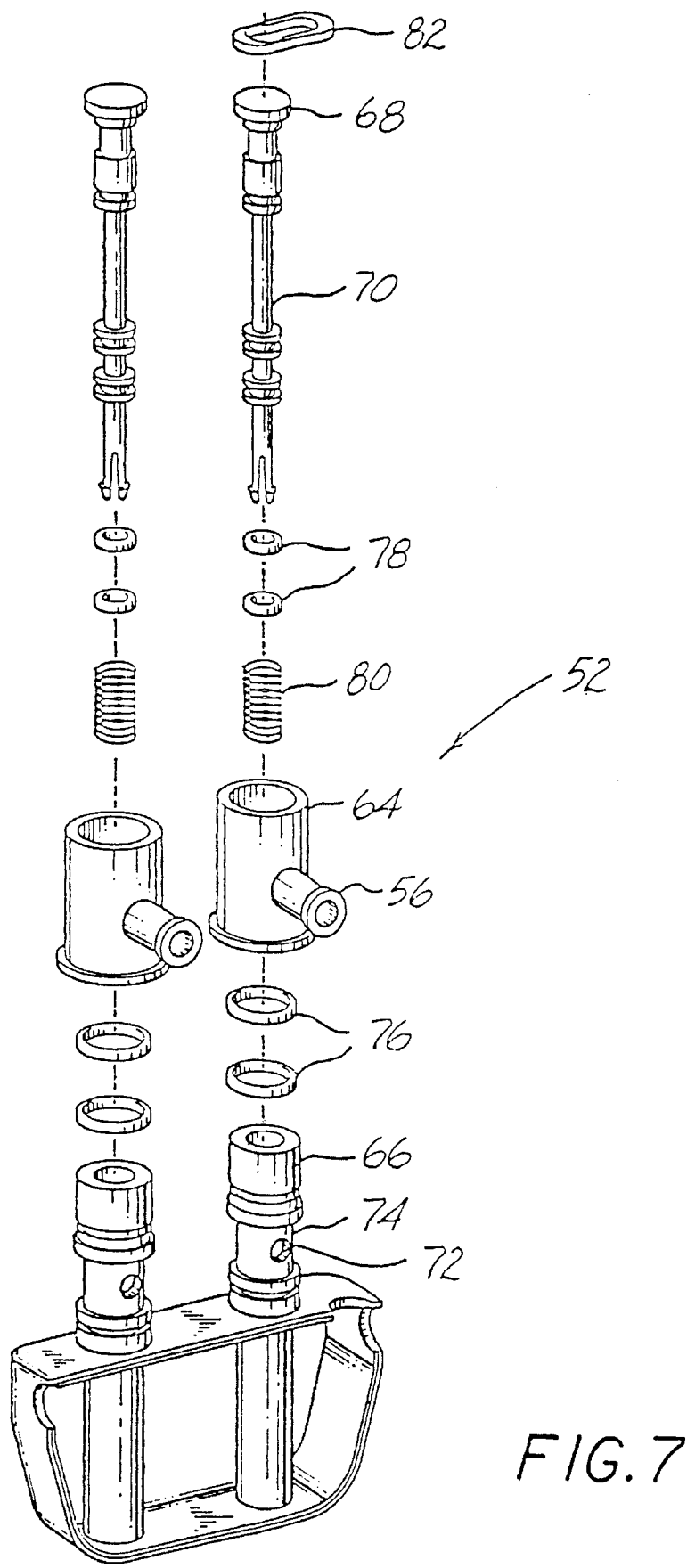
FIG. 7 illustrates an exploded perspective view of the valve mechanism of the device of FIG. 5.

Referring now in specific detail to the drawings, in which like reference numerals identify similar or identical elements throughout the several views, FIG. 1 shows the endoscopic surgical instrument for aspiration and irrigation according to the present invention. Instrument 10 comprises a body portion 12 to which at least a pair of valve members 14 and 18 are attached. Preferably, at least one valve member, namely valve member 14, includes a rotatable connection port 16 for coupling a source of irrigation or a source of suction thereto. The function of rotatable connection port 16 will be discussed below. Valve member 18 may include a rotatable connection port; however, in a preferred embodiment valve member 18 includes a rotatably lockable actuator 18a for maintaining a source of constant irrigation or suction. Connection port 20 is controlled by valve member 18.

Body portion 12 essentially comprises a mixing chamber which communicates with both connection port 16 and connection port 20 through valve member 14 and 18, respectively. Body portion 12 extends into coupling member 22 which couples the mixing chamber within body portion 12 with a single lumen cannula 24. Single lumen cannula 24 provides a means for transporting the irrigation fluid or the suction force from their respective sources to the surgical site. Single lumen cannula 24 simplifies the construction of device 10 and significantly reduces cost in that a single tubular member having a reduced diameter single channel therethrough is utilized to carry both the suction and irrigation fluid to the surgical site.

Preferably, single lumen cannula 24 is enclosed within outer sleeve member 26 which concentrically surrounds and contacts single lumen cannula 24 along its length and is slidable in a longitudinal direction by grip member 28. The purpose of the slidable outer sleeve will be discussed below.

Device 10 may further include a bayonet-type connector 30 for providing electrocautery capabilities to device 10. Bayonet connector 30 is in electrical contact with single lumen cannula 24 through the provision of bus bar 32. Bayonet connector 30 provides for cauterization at the surgical site and for electrodissection of tissue. Device 10 may further include laser dissection means, which may be provided by an optical fiber through optical fiber port 34.

FIG. 2 illustrates the device of FIG. 1 enclosed in a working housing 36 which provides for gripping and handling of device 10. Housing 36 may be provided with scored portion 38 in one or several locations to facilitate gripping. As is seen in FIG. 2, single lumen cannula 24 is enclosed by outer sleeve member 26 which is slidable between a proximal position whereby apertures 44 are exposed at the distal end 42, to a distal position where outer sleeve 26 covers apertures 44. A hydrodissection tip 40 is shown as connected to the distal end 42 of single lumen cannula 24. In use, device 10 may be utilized for hydrodissection purposes. In such a case, a high pressure irrigation fluid source is utilized and connected, preferably to either of connection port 16 or connection port 20. As the irrigation fluid exits the aperture 41 at the end of hydrodissection tip 40, the pressure at which the fluid exits may be regulated and varied by sliding outer sleeve 26 in the direction of arrow A to cover one or more of apertures 44. Covering apertures 44 will increase the pressure of the fluid exiting tip 40 to provide for greater or less pressure of the irrigation and dissection fluid.

Preferably, outer sleeve 26 is constructed of an electrical insulating material, such as plastic, or may be provided with an electrically insulating shrink tubing, so that when device 10 is used for electrocautery purposes, the risk of shock is mitigated. FIG. 3 shows the electrical connection of bayonet connector 30 with single lumen cannula 24 at connection point 46.

FIG. 4 illustrates a rear view of the device of FIG. 2 which illustrates connection port 20 as being in axial alignment with valve members 14 and 18, while optical fiber port 34 is in direct axial alignment with single lumen cannula 24. Optical fiber port 34 is provided with a sealing means 48 which generally comprises a rubber type gasket which is penetrable by the optical fiber and seals around the fiber to prevent loss of suction pressure and leakage of irrigation fluid.

FIGS. 5 and 6 illustrate an alternate embodiment 50 of the instrument of FIG. 1. Instrument 50 comprises a pair of rotatable trumpet valve members 52 which are secured to a body portion 60 and are positioned directly in line with a coupling member 62 which extends into the single lumen cannula described above. An optical fiber port 58 is provided which is directly in line with coupling member 62. Rotatable trumpet valve members 52 include rotatable connection ports 56 whose function will be discussed below.

Turning to FIG. 7, there is shown the rotatable trumpet valve members 52 (as well as valve member 14 discussed above in connection with FIG. 1). Valve members 52 essentially Comprise a rotatable outer housing 64 to which connection port 56 is coupled. Outer housing 64 fits over inner housing 66, and valve stem 70 of actuator knob 68 extends through the inner and outer housings. Inner housing 66, is provided with an opening 72 which communicates a chamber as defined by the inner wall of outer housing 64 and chamber wall 74 to allow for the passage of fluid or suction pressure upon actuation of valve member 52. A pair of gaskets 76 are provided which seal the top and bottom of the chamber between the outer housing 64 and the inner housing 66, to prevent leakage while maintaining the rotatable feature. A second pair of gaskets 78 are secured to stem 70 for actuation of valve member 52. A spring means 80 is provided, as is common in trumpet-type valves. In addition, a locking ring 82 may be provided to maintain the valve in the continuously on position. The locking ring may be eliminated such as shown in FIG. 1, where a camming surface is provided on the interior surface of actuator knob 18a which engages a cam surface on the outside of outer housing 64.

Figure 8:
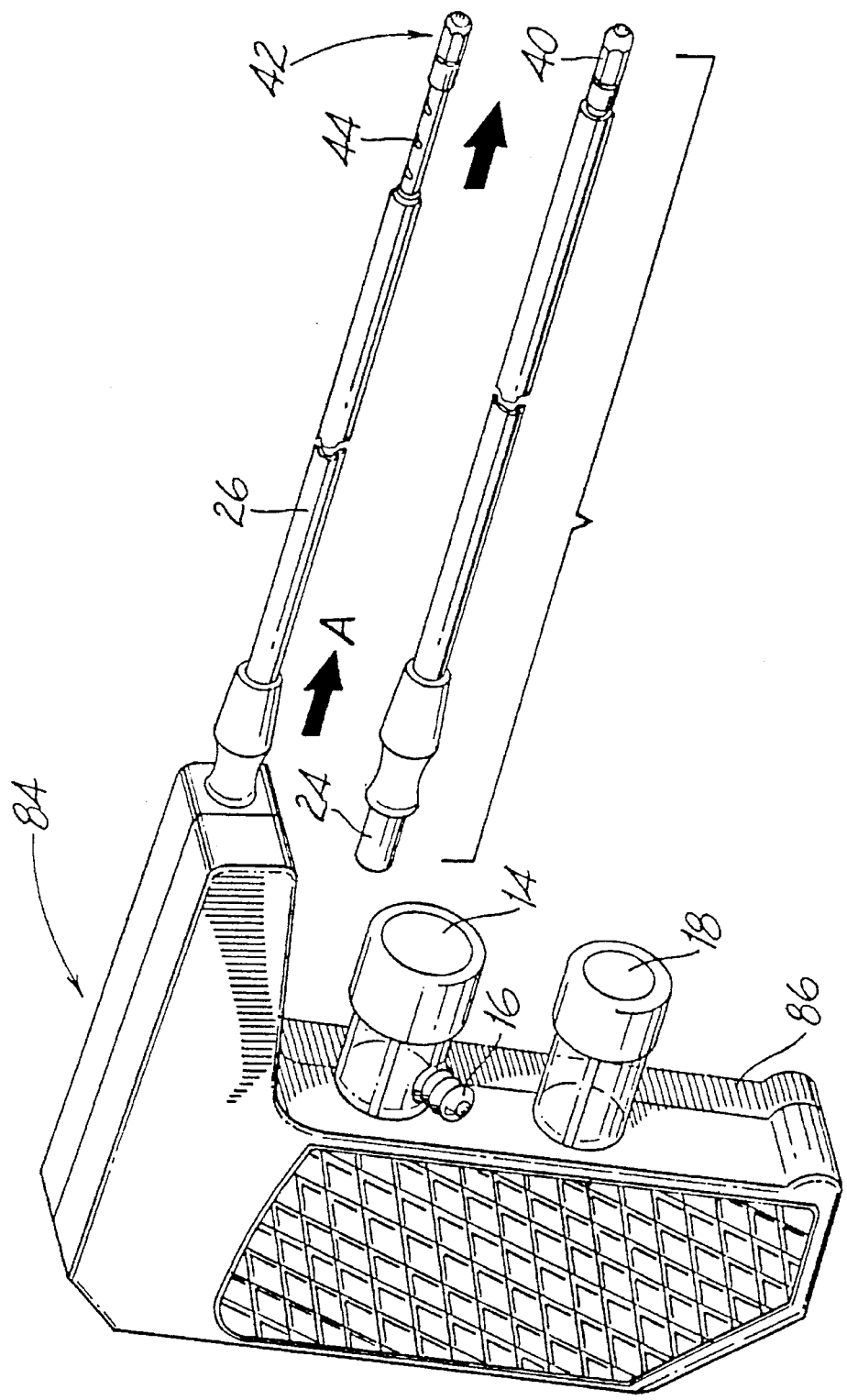
FIG. 8 illustrates a perspective view of a second embodiment of the outer enclosure employing the device of FIG. 1 according to the present invention.
Figure 10:
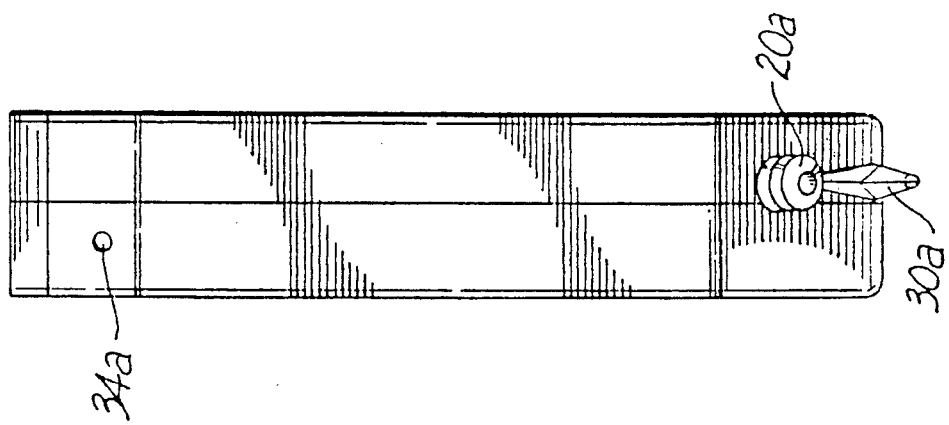
FIG. 10 illustrates a rear plan view of the device of FIG. 8.

Turning now to FIG. 8, there is illustrated a further embodiment of the surgical instrument for aspiration and irrigation according to the present invention, in which a pistol-type housing 86 is provided. Housing 86 encloses device 10a and includes valve members 14 and 18, where valve member 14 includes rotatable connection port 16. Extending from housing 86 is single lumen cannula 24 which includes an outer sleeve member 26 longitudinally slidable in the direction of arrow A in the manner described above. FIG. 10 illustrates a rear view of the device of FIG. 8 which shows the optical fiber connection port 34a as well as connection port 20a and bayonet connector 30a.

Figure 9:
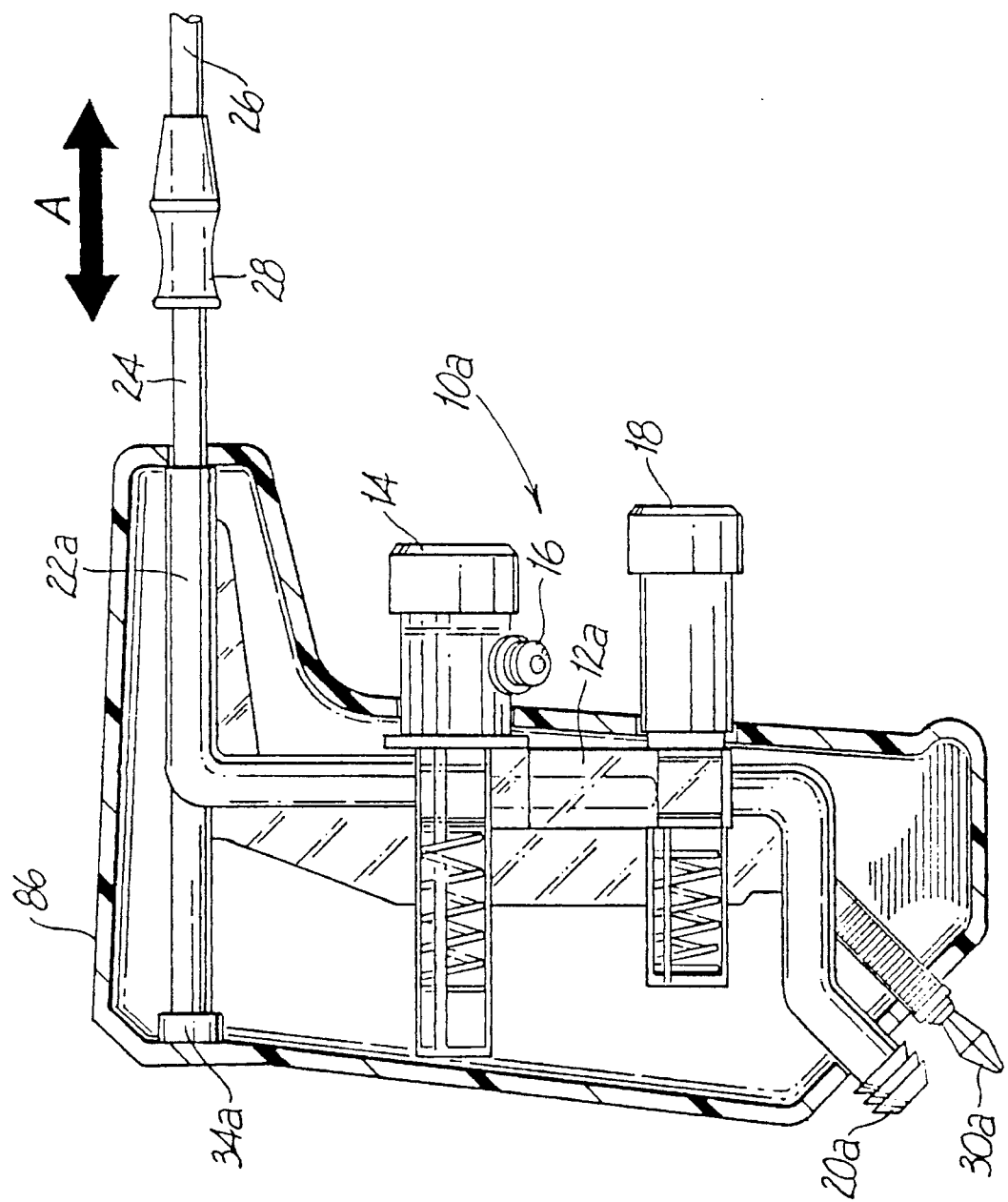
FIG. 9 illustrates a side plan view in partial cross section of the device of FIG. 8.

FIG. 9 illustrates surgical instrument 10a enclosed in housing 86. Connection port 20a extends in a rearward direction from body portion 12a and exits the device as shown. Coupling member 22a is provided as shown which engages body portion 12a and single lumen cannula 24, and further includes means to connect optical fiber port 34a in direct axial communication with single lumen cannula 24. Outer sleeve member 26 is slidable in a longitudinal direction in the direction of arrow A through the provision of grip member 28.

Figure 11:
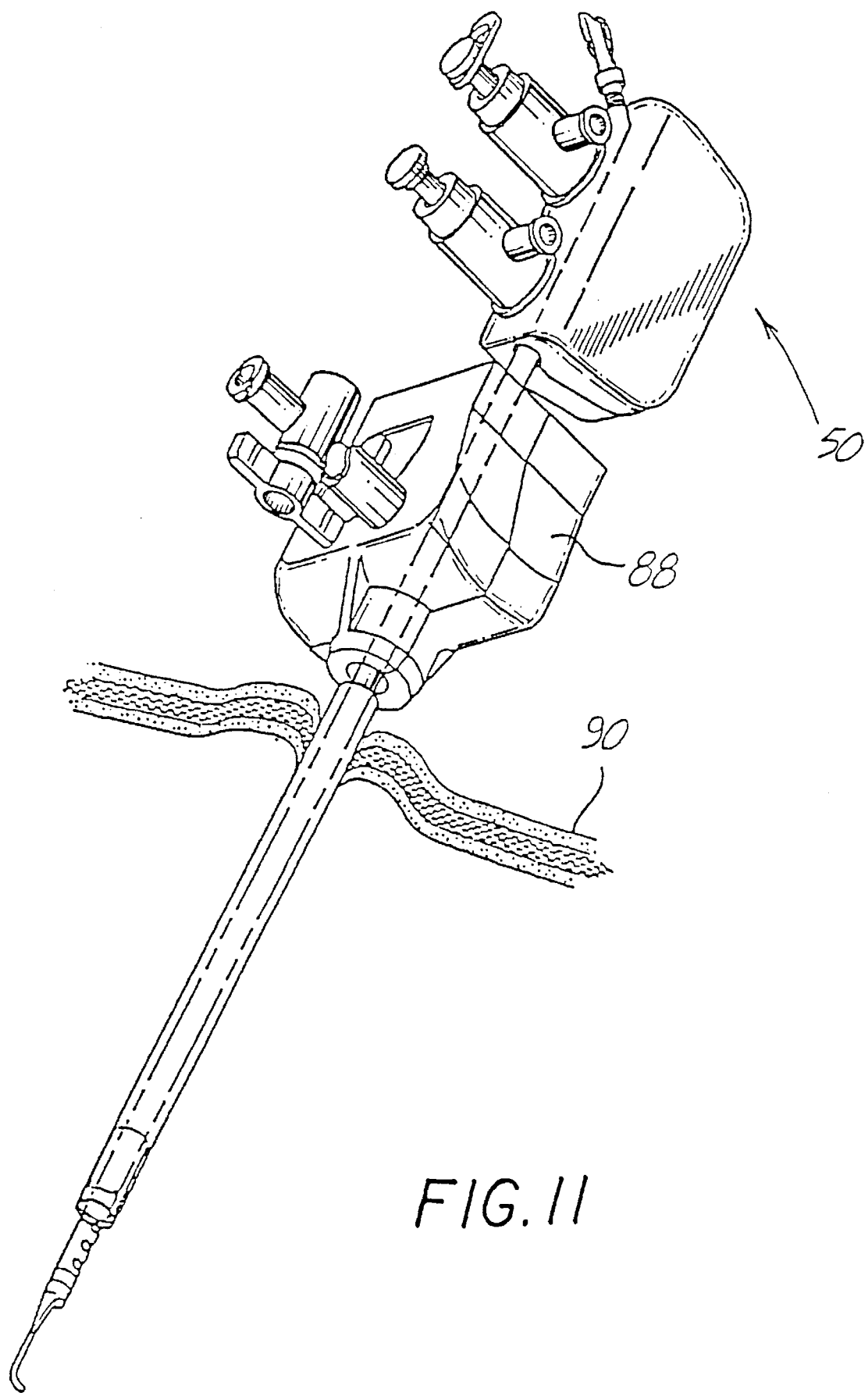
FIG. 11 illustrates a perspective view of the endoscopic surgical instrument for aspiration and irrigation according to the present invention in use during a surgical procedure.

FIG. 11 illustrates the suction and irrigation device 50 according to the present invention in use at a surgical site. The body wall 90 of the patient is penetrated by a trocar assembly, the cannula 88 of which remains in place after the pointed obturator has been remove. Instrument 50 is inserted to the surgical site through cannula 88 as shown to perform the surgical procedure.

FIGS. 12a and 12b illustrate a novel means for connecting the working tip of the device of the present invention to the single lumen cannula. The tips may be interchangeable and may include a plurality of tips such as that shown in FIGS. 12a and 12b, as well as FIGS. 13a through 13c and FIGS. 14a through 14c. As shown in FIGS. 12a and 12b, key slots 92 are provided at the distal end 42 of single lumen cannula 24 for accepting the key posts 96 of dissector tip 94. Tip 94 is secured through a sealing gasket 98 to key slots 92. Dissector tip 94 includes a central passageway 100 to maintain fluid Communication with the interior of single lumen cannula 24 adjacent the working tip 102. Tip 102 may further include a knife 104 as shown in FIG. 14c.

An alternate means of securing detachable dissector tip 94 to distal end 42 of single lumen cannula 24 may be accomplished through the provision of coupling members 95 and 97 as shown in FIGS. 15 and 16. In this embodiment, an annular groove 106 is provided which engages a detent on the interior of distal end 42 to snap fit coupling members 95 and 97 therein. In addition, a threaded connection may be used.

In addition, detachable tips 94 may be quickly and releasably secured to distal end 42 by means shown in FIGS. 25a–b and 26a–b. In FIGS. 25a–b, distal end 42 includes external screw threads 93, which mate with internal threads on tip 94 (not shown). Alternately, as shown in FIGS. 26a–b, tip member 94 may include a spring clip 110 having a deflectable post 112. Post 112 snap fits into recess 114 in distal end 42.

A further feature of the present invention provides a plurality of interchangeable tip members for connection at the distal end 42 of the suction and irrigation device 10. The interchangeable tips allows the surgeon to choose the proper working tool for the particular surgical procedure in which he is involved. To this end, the present invention provides a dispensing device 200 which includes a plurality of tips which are accessible to the surgeon at his desire.

Figure 18:
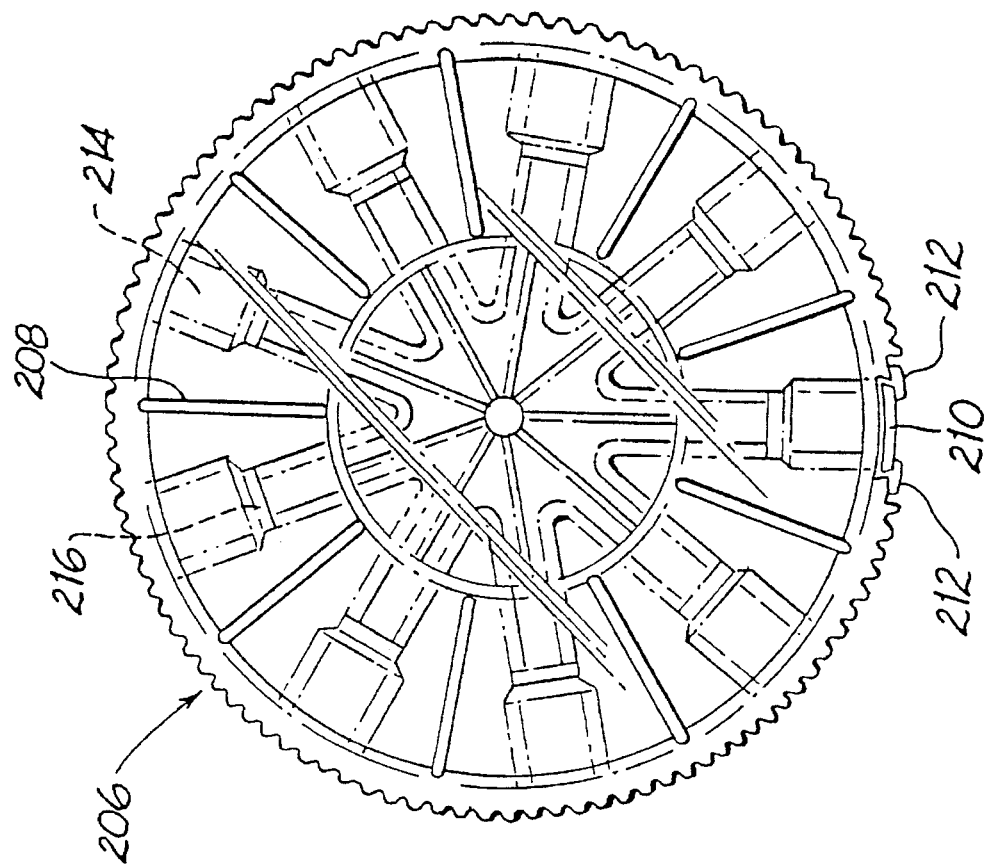
FIG. 18 illustrates a bottom plan view of the dispenser of FIG. 17.
Figure 17:
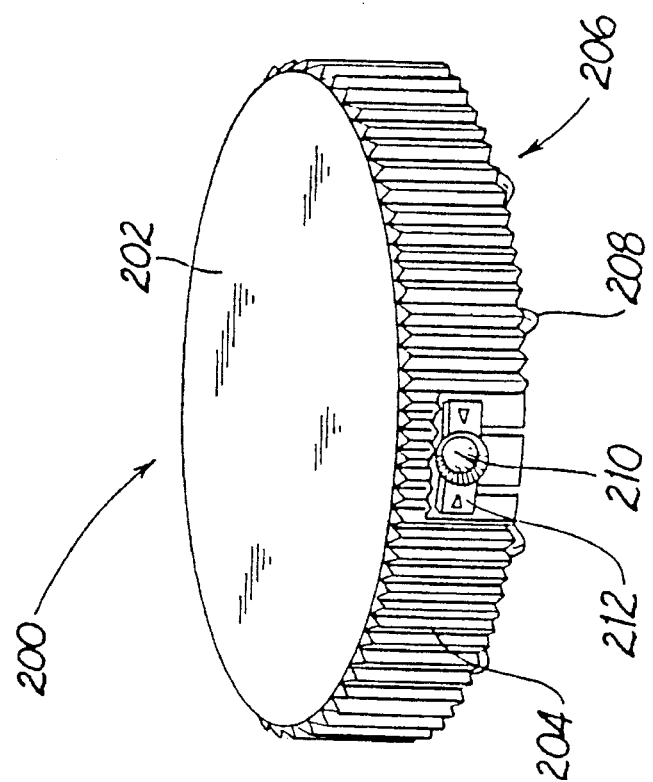
FIG. 17 illustrates a perspective view of a first embodiment of a tip dispenser for use with the surgical instrument of the present invention.

As best seen in FIG. 17, dispenser 200 comprises a disc-shaped body having a top cover 202 and side wall 204, in which an access opening 210 is provided. The dispenser bottom is also a disc-shaped member 206 as best seen in FIG. 18, and is provided with a plurality of rib members 208 which allows the surgeon to rotate the dispenser bottom 206 within top cover 202 to align tool recesses 214 with access opening 210. The device may be operated with a single hand whereby the surgeon rotates the dispenser bottom 206 by pushing along ribs 208 to rotate the proper tool in a recess 214 into alignment with the access opening 210. Also provided on side wall 204 are alignment means 212 which allows the surgeon to locate the access opening without having to look at the dispenser 200.

In use, when the surgeon chooses which tip he desires for the particular surgical procedure, dispenser bottom 206 is rotated until that particular tip in a recess 214 is in alignment with opening 210. Opening 210 has a dimension such that it is wide enough for the insertion of the distal end 42 of the surgical instrument 10. Once inserted, the tip may be removed upon securement of the tip onto the distal end 42, such as by snap fit or rotation onto threads 93 provided on the distal end 42, or other suitable means. Once secured to the distal end 42 instrument 10, the tool tip may be removed through access opening 210. The process is reversed to return the tool tip to a vacant recess in dispenser bottom 206. As best seen in FIG. 18, locking means 216 are provided for a frictional fit to hold the tip members in place inside the dispenser.

FIGS. 19–20 illustrate an alternate embodiment of the dispenser of FIG. 17. Dispenser 220 is similar to dispenser 200 except for the provision of a single outside wall 224 which forms the outer housing. Dispenser body 222 is similar to dispenser bottom 206 except for the provision of a single non-linear rib member 230 which traverses the diameter of the dispenser body 222. Rib member 230 provides a larger gripping surface for the surgeon to rotate dispenser body 222 within housing 224. Housing 224 is provided with an access opening 228 similar to access opening 210 described above, and further may include alignment means 226 to provide for the surgeon's feeling for the opening.

Turning to FIGS. 20a and 20b, it can be seen that dispenser body 222 includes a plurality of tool recesses 236 to accommodate a number of tool tips. In this embodiment, each of the recesses is provided with an index notch 234 which will mate with index detent 232 provided adjacent access opening 228 on housing 224 when the dispenser body is rotated to the proper position wherein access opening 228 is in alignment with opening 227 in the respective chamber. This provides a tactile indicator to allow the user to find a recess without having to look at the dispenser 220, during rotation of dispenser body 222 within housing 224. Similar to dispenser 200 above, frictional locking means 238 are provided to hold the tool members in place within the tool recesses 236.

In addition to the indexing means shown in FIG. 20a, an indexing mechanism is provided as shown in FIG. 20b to indicate to the user that the dispenser is closed. A single closed position index notch 240 may be provided on the outer perimeter of the dispenser body 222 as shown in between two or more of the recesses 236. This allows index detent 232 to engage index notch 240 to ensure that the dispenser is in a closed position and none of the tools within the tool recesses 236 may be accessed. Clearly, a plurality of index notches could be provided each disposed between adjacent recesses 236. The notch and detent can optionally be dimensioned to provide a lock to prevent inadvertent rotation of the dispenser such as during shipping. Other locking mechanisms are also contemplated.

Figure 21:
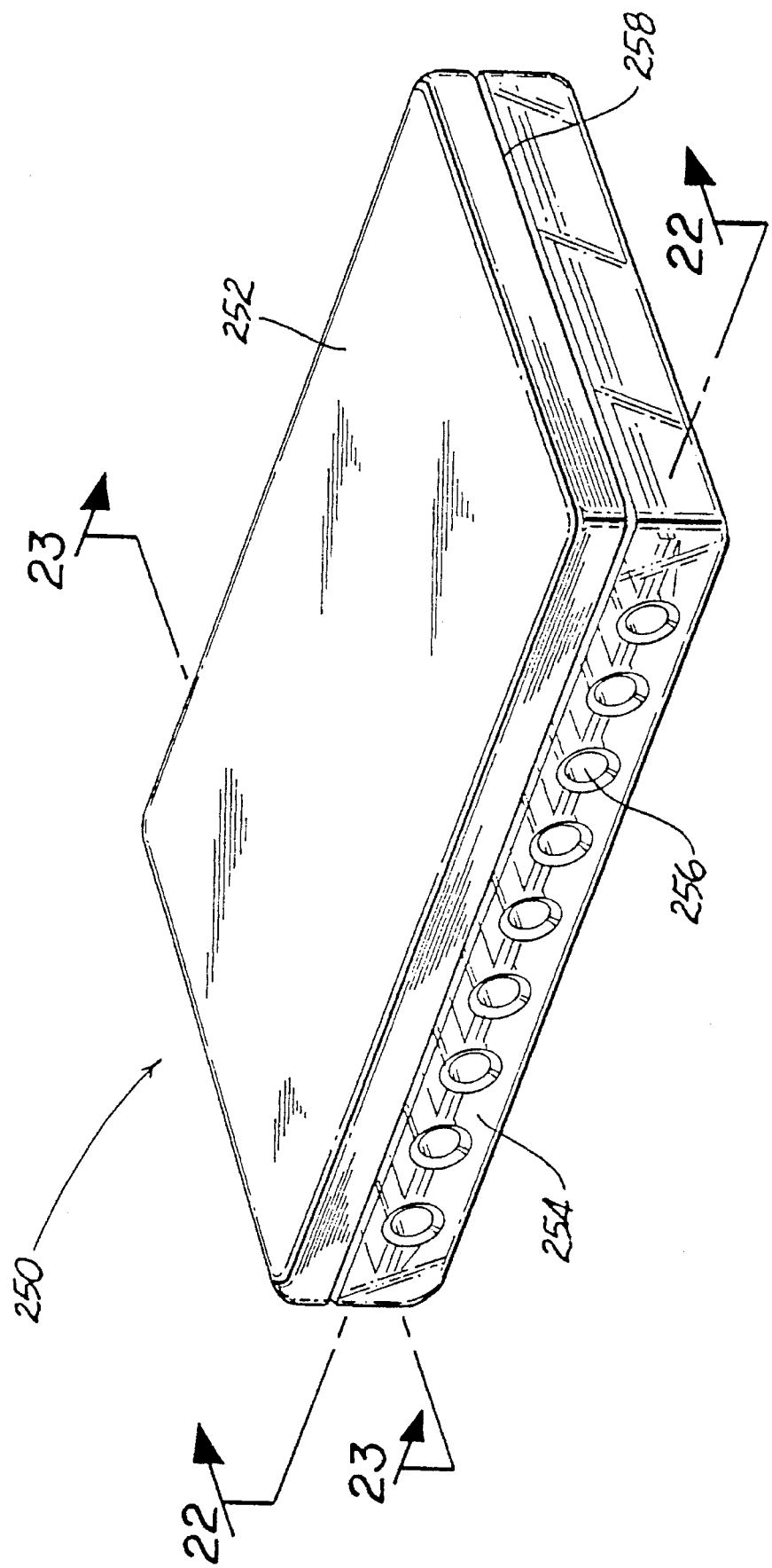
FIG. 21 illustrates a perspective view of a third embodiment of a tip dispenser according to the present invention.

FIG. 21 illustrates a third embodiment of the dispenser of the present invention. Dispenser 250 comprises a top cover 252 which overlays a bottom housing 254 in a floating-type arrangement. Bottom housing 254 is provided with a plurality of access openings 256 which provide access to tool tips positioned therein. A channel 258 is provided between top cover 252 and bottom housing 254 to allow for the "floating" feature, which will be described below.

Figure 22:
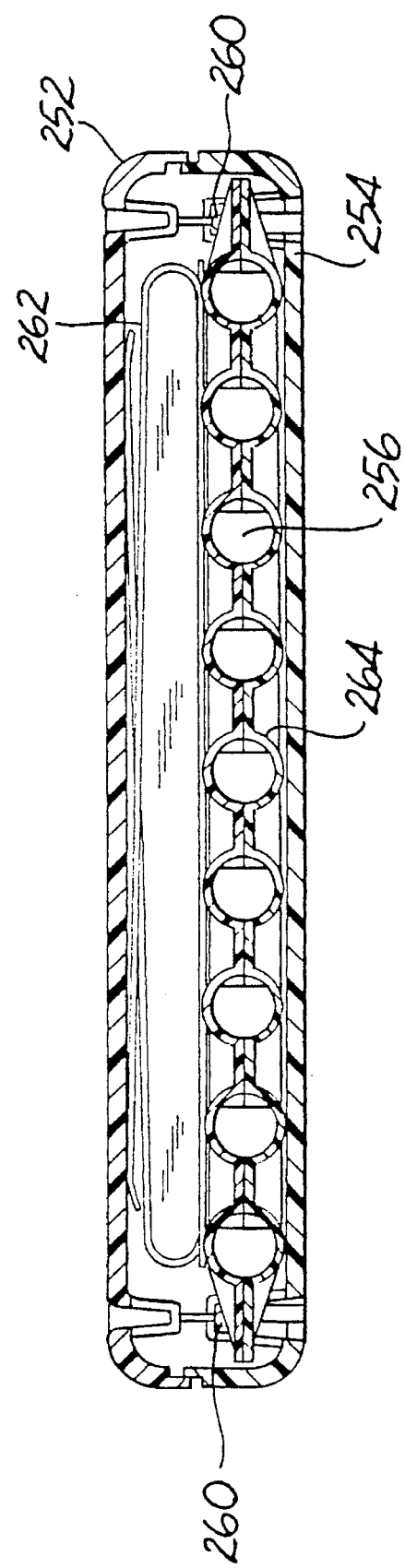
FIG. 22 illustrates a cross;sectional view taken along lines 22—22 of FIG. 21 of the dispenser of FIG. 21.

FIG. 22 illustrates a cross-sectional view of the dispenser 250 taken along lines 22–22 of FIG. 21. As shown, top cover 252 is secured to bottom housing 254 and floating connection point 260, which allows top cover 252 to be pushed towards bottom housing 254 to provide for manipulation of a tool member during use. Access openings 256 are formed by an internal tool frame 264 which is secured to bottom housing 254. A leaf spring member 262 is provided which facilitates the floating connection.

Figure 23:
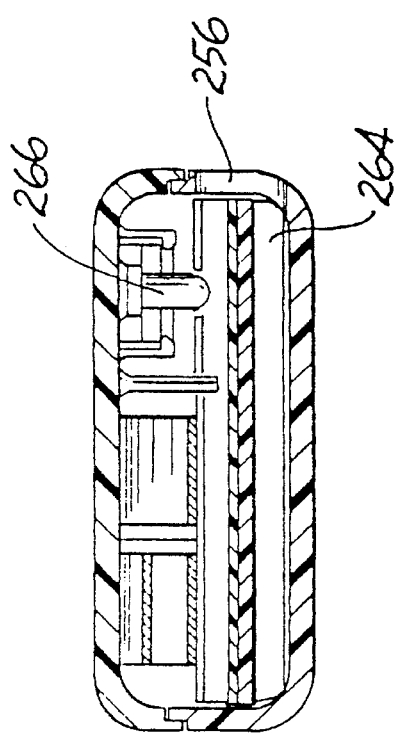
FIG. 23 illustrates a cross:sectional view taken along lines 23—23 of FIG. 21 of the dispenser of FIG. 21.

FIG. 23 illustrates a side cross-sectional view taken along lines 23—23 of FIG. 21. As shown, internal tool frame 264 is aligned with access opening 256, and each of the openings 256 in internal tool frame 264 includes the provision of a release pin 266. The function of this device will now be described.

Top cover 252 is spring biased away from bottom housing 254 by leaf spring 262. The top cover includes release pin 266 which will engage spring clip 112 positioned on tool member 94 as best seen in FIGS. 26a and 26b. Spring clip 112 is aligned with release pin 266 but is not engaged by release pin 266 when the tip is in access opening 256. In order to remove a tip from one of the access opening 256, the surgical instrument is inserted into the dispenser so that the spring of the selected tip engages the recess 114 as shown in FIG. 26b. Since the top cover 252 is biased away from the bottom housing 254, release pin 266 does not interfere with the spring. However, when it is desired to return the tip to the dispenser, top cover 252 is manually pushed towards bottom housing 254 so that release pin 266 engages spring clip 112 and pushes it out of recess 114 to disengage the instrument.

Figure 24:
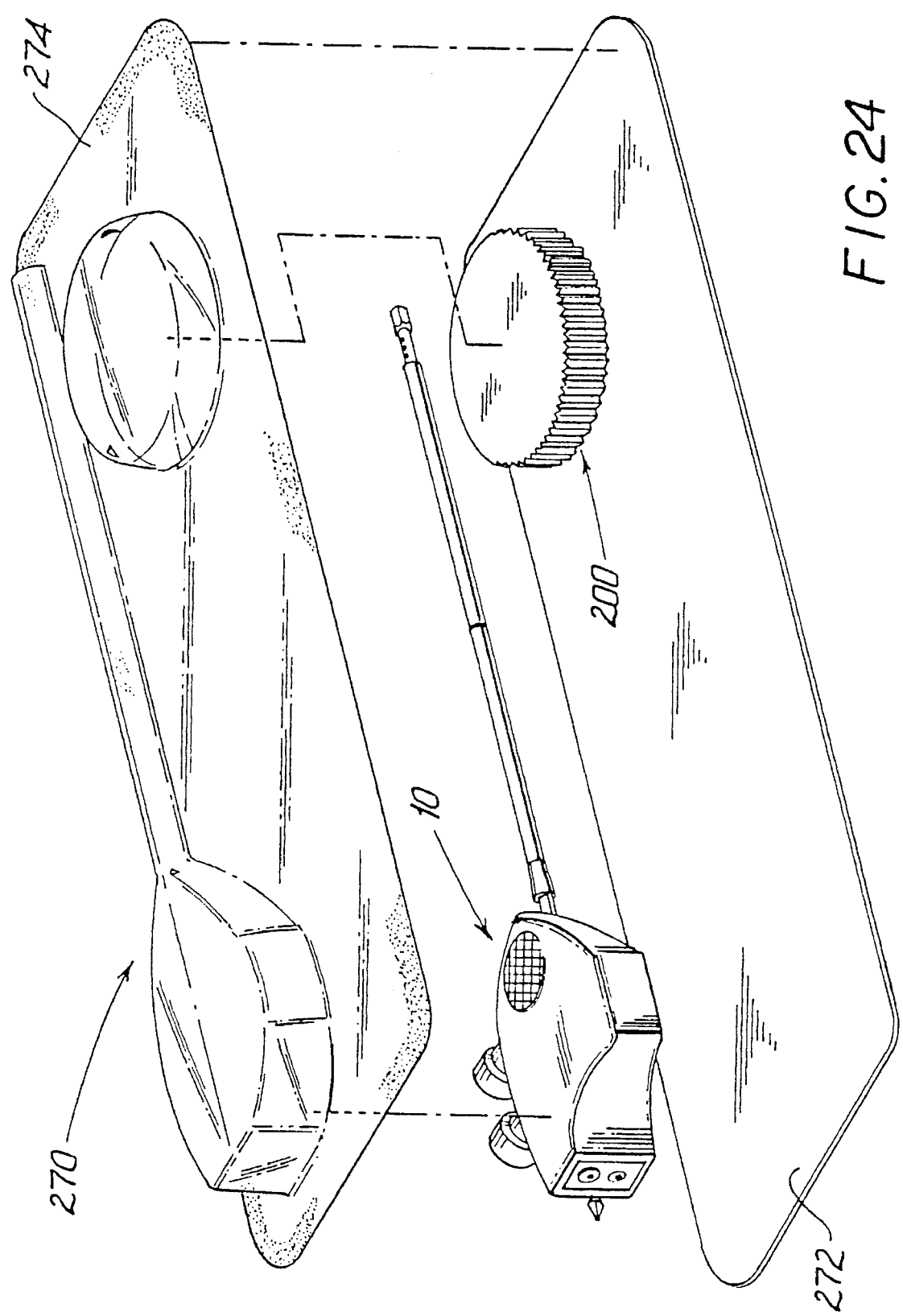
FIG. 24 illustrates a perspective view of a package or kit enclosing the surgical instrument and the dispenser according to the present invention.

Turning now to FIG. 24, it is contemplated that the present invention include a kit which comprises surgical instrument 10 and at least dispenser 200. This allows the surgeon during a surgical procedure to have the proper tool and its proper accessories which are positioned within dispenser 200. Kit 270 preferably comprises at least surgical instrument 10 and dispenser 200 packaged in a vacuum formed top cover 274 preferably formed of plastic, and a bottom sheet of fibrous material such as spun bonded polyolefin fibers, commonly known as Tyvek (a trademark of DuPont).

Figure 27A:
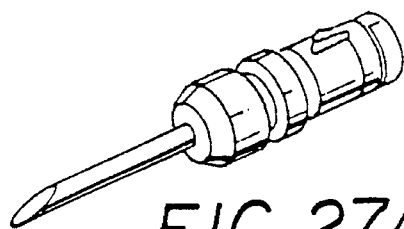
FIG. 27 illustrates a perspective view of various tool mechanisms which can be stored in the dispenser of the present invention.
Figure 27E:
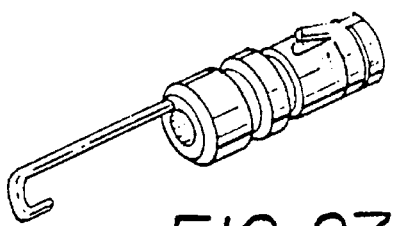
Figure 27B:
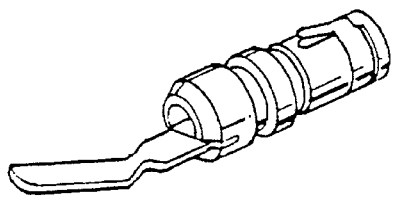
Figure 27F:
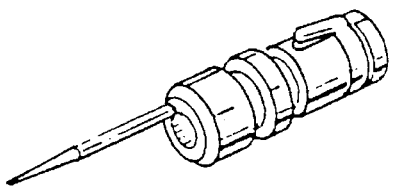
Figure 27C:
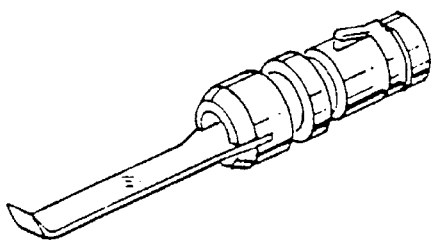
Figure 27G:
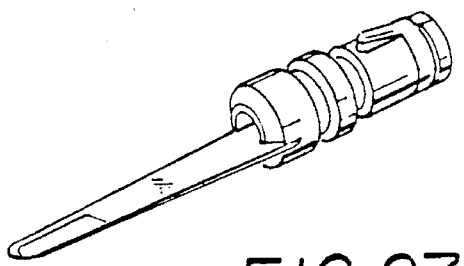
Figure 27D:
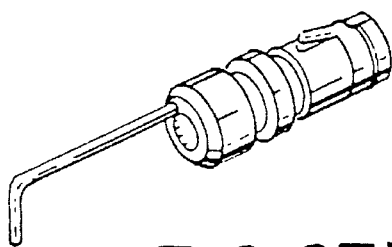
Figure 27H:
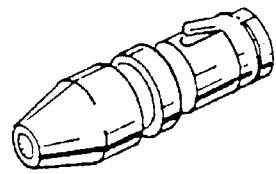
Figure 27I:
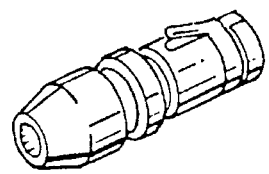

FIGS. 27a–27i illustrate examples of several of the tip members which may be housed in the dispenser of the present invention, such as J-hook, aqua dissector, aspiration tip, micro tautcry tip, straight scalpel, L-hook, laser guide, spatula and 60° knife. Each tip includes means for coupling the tool tip to a surgical instrument; in these figures spring clip 112 is shown. The tips include electrocautery capabilities, and in particular FIGS. 27a, 27d, 27e and 27f each show cautery tips. FIG. 27b illustrates a spatula, FIG. 27c illustrates a blunt dissector, while FIG. 27g shows a knife. FIGS. 27h and 27i each show hydrodissection nozzles.

In use, the instrument of the present invention provides a variably orientable aspiration and irrigation device which may also be used for dissecting tissue. The instrument is constructed to accommodate use with either hand and at any orientation to the patient's body during the surgical procedure through the provision of rotatable valve members which are at least 180° rotatable so that the connection hoses to the irrigation and aspiration sources may be oriented on either side of the device. Furthermore, the connection ports for at least an optical fiber for laser surgery purposes as well as a bayonet connection member for electro-cautery procedures are provided substantially parallel to the longitudinal axis of the single lumen cannula which communicates the instrument with the surgical site. In addition, one of the rotatable valve members may be replaced by a locking valve member and the connection port thereto extends directly from the distal end of the device in parallel with the longitudinal axis of the single lumen cannula.

While the invention has been particularly shown and described with reference to the preferred embodiments, it will be understood by those skilled in the art that various modifications and changes, in form and detail may be made therein without departing from the scope and spirit of the invention. Accordingly, modifications such as those suggested above, but not limited thereto, are to be considered within the scope of the invention.

What is claimed is:

1. A surgical accessory dispenser for surgical instrumentation comprising:

a housing having at least two parts secured to each other, a first part being movable with respect to a second part;

a plurality of chambers disposed within said housing for accommodating a surgical accessory in each of said chambers;

said housing having at least one opening for accessing each of said chambers;

means for releasably securing a surgical accessory in each of said chambers to permit removal of said accessory; and means for uncoupling said accessory from a surgical instrument to permit re-loading of said accessory into said housing said means for uncoupling bring actuated by moving said first part of said housing with respect to said second part of said housing;

wherein said at least one opening permits loading and unloading of said surgical accessory into each of said chambers.

2. A surgical accessory dispenser according to claim 1, wherein said first part of said housing defines a top portion and said second part defines a bottom portion, said housing having a plurality of openings defining said chambers, and said uncoupling means comprises a plurality of post members extending from an inside surface of said top portion in a direction towards an inside surface of said bottom portion and movable from a position outside said openings to a position within said openings such that said post members engage a portion of said surgical instrument to release said accessory.

3. A surgical accessory dispenser according to claim 1, wherein said first part of said housing defines a top portion movably coupled to said second part which defines a bottom portion, said top portion being spring biased away from said bottom portion and movable towards and away from said bottom portion.

4. A surgical accessory dispenser according to claim 3, further comprising a chamber element including plurality of chambers, said chamber element being positioned with said housing between said top and bottom portions and frictionally securing said accessories in said dispenser.

5. A surgical accessory dispenser according to claim 4, wherein said top portion of said housing is spring biased away from said chamber element.

6. A surgical accessory dispenser according to claim 5, further comprising a surgical accessory at least partially disposed in at least one of said chambers, wherein said accessory is removable from said chamber when said top portion is biased away from said bottom portion.

7. A surgical accessory dispenser according to claim 5, further comprising a surgical accessory at least partially disposed in at least one of said chambers, wherein said top portion is movable toward said bottom portion against said spring bias, said top portion including means for uncoupling said accessory from a surgical instrument positioned in said chamber.

8. A surgical accessory dispenser according to claim 7, wherein said housing includes a plurality of openings defining said chambers, and said means for uncoupling comprises a plurality post members depending from said top portion towards said bottom portion and movable from a position outside said openings to a position within said openings such that said post members are moved into contact with an accessory when said top portion is moved toward said bottom portion.

9. A surgical accessory dispenser according to claim 1, wherein said surgical accessory includes a tool member for an endoscopic surgical instrument, said tool member having a body portion and a coupling portion for retaining said tool member in one of said chambers.

10. A surgical accessory dispenser according to claim 9, wherein said coupling portion of said tool member comprises a leaf spring.

11. A surgical accessory dispenser comprising:

a generally disc-shaped housing having an upper portion rotatably overlaying a lower portion, said upper portion having an opening to access said lower portion, wherein said lower portion includes a plurality of radially inwardly directed chambers for accommodating surgical accessories, said chambers being open to an outer perimetric wall of said disc shaped housing and being aligned sequentially with said opening in said upper portion upon rotation of said upper portion to access said accessories positioned therein.

12. A surgical accessory dispenser according to claim 11, further comprising indexing means for aligning said chambers with said opening.

13. A surgical accessory dispenser according to claim 12, wherein said indexing means includes a detent on said upper portion and a plurality of notches on said lower portion associated with said plurality of chambers, such that a notch corresponds to each of said chambers.

14. A surgical accessory dispenser according to claim 13, wherein detent on said upper portion is aligned with the center of said opening.

15. A surgical accessory dispenser according to claim 11, wherein said upper portion has a knurled surface on an outer perimetric wall to facilitate rotation about said lower portion.

16. A surgical accessory dispenser according to claim 11, wherein said upper portion has an outer diameter slightly larger than an outer diameter of said lower portion.

17. A surgical accessory dispenser comprising:

a generally disc-shaped housing having a plurality of radially inwardly directed chambers opening from a perimetric wall of said housing for accommodating surgical accessories; and a continuous band member overlaying said perimetric wall of said housing and being rotatable with respect to said housing;

wherein said band member includes an opening to provide access to said chambers and said accessories positioned therein.

18. A surgical accessory dispenser according to claim 17, further comprising indexing means for aligning said opening with each of said chambers.

19. A surgical accessory dispenser according to claim 18, wherein said indexing means includes a detent on said band member associated with said opening, and a plurality of notches on said housing, such that each notch corresponds to one of said chambers.

20. A surgical accessory dispenser according to claim 17, wherein said band member has a diameter slightly larger than an outer diameter of said housing, said housing being rotatable within said band member.

21. A surgical accessory dispenser according to claim 17, further comprising means for retaining said accessories in said chambers.

22. A surgical accessory dispenser according to claim 21, wherein said retaining means comprises at least one boss member for frictionally engaging said accessories.

* * * * *